United States Patent
Kovacs et al.

(10) Patent No.: US 10,687,831 B2
(45) Date of Patent: Jun. 23, 2020

(54) REAMER AND GUIDE FOR GLENOID AUGMENT PREPARATION

(71) Applicant: Biomet Manufacturing, LLC, Warsaw, IN (US)

(72) Inventors: Michael Francis Kovacs, Warsaw, IN (US); Nathan A. Winslow, Warsaw, IN (US); Michael Dziekan, Warsaw, IN (US); Donald W. Dye, Warsaw, IN (US); Thomas Michael Vanasse, Gainesville, FL (US); Robert J. Taylor, Elkhart, IN (US); Lawrence Gulotta, Chappaqua, NY (US)

(73) Assignee: Biomet Manufacturing, LLC, Warsaw, IN (US)

( * ) Notice: Subject to any disclaimer, the term of this patent is extended or adjusted under 35 U.S.C. 154(b) by 184 days.

(21) Appl. No.: 15/643,951

(22) Filed: Jul. 7, 2017

(65) Prior Publication Data
US 2018/0008293 A1 Jan. 11, 2018

Related U.S. Application Data

(60) Provisional application No. 62/360,127, filed on Jul. 8, 2016, provisional application No. 62/374,222, filed on Aug. 12, 2016.

(51) Int. Cl.
*A61B 17/17* (2006.01)
*A61B 17/16* (2006.01)
*A61F 2/46* (2006.01)

(52) U.S. Cl.
CPC ...... *A61B 17/1778* (2016.11); *A61B 17/1659* (2013.01); *A61B 17/1684* (2013.01); *A61F 2/4612* (2013.01)

(58) Field of Classification Search
CPC ............. A61B 17/1778; A61B 17/1684; A61F 2/4612
See application file for complete search history.

(56) References Cited

U.S. PATENT DOCUMENTS

2005/0049601 A1 3/2005 Keller
2010/0082031 A1 4/2010 Sackett et al.
(Continued)

FOREIGN PATENT DOCUMENTS

CN 109561900 A 4/2019
DE 102008053566 6/2009
(Continued)

OTHER PUBLICATIONS

"Australian Application Serial No. 2017293923, First Examination Report dated Apr. 10, 2019", 4 pgs.
(Continued)

*Primary Examiner* — David W Bates
(74) *Attorney, Agent, or Firm* — Schwegman Lundberg & Woessner, P.A.

(57) ABSTRACT

The present disclosure provides reaming apparatuses. The reaming apparatuses can comprise a base guide, a reamer, and a reamer driver. The base guide can define a base guide through bore and a base guide articulating surface. The base guide articulating surface can be oriented at an angle relative to the base guide through bore. The reamer can define a reamer articulating surface operable to allow rotation of the reamer on the base guide articulating surface. The reamer driver can operate with the reamer to cause rotation of the reamer when the reamer driver rotates.

20 Claims, 12 Drawing Sheets

(56) References Cited

U.S. PATENT DOCUMENTS

| | | | | |
|---|---|---|---|---|
| 2011/0213371 | A1* | 9/2011 | Anthony | A61B 17/1659 606/85 |
| 2013/0096564 | A1* | 4/2013 | Winslow | A61B 17/1739 606/96 |
| 2014/0107652 | A1* | 4/2014 | Walker | A61B 17/15 606/81 |
| 2015/0265288 | A1* | 9/2015 | Guederian | A61B 17/1684 606/80 |
| 2015/0374502 | A1* | 12/2015 | Hodorek | A61B 17/17 623/19.11 |
| 2016/0045207 | A1* | 2/2016 | Kovacs | A61B 17/1684 606/80 |
| 2016/0074047 | A1* | 3/2016 | Fritzinger | A61B 17/162 606/80 |
| 2018/0280037 | A1* | 10/2018 | Dassonville | A61B 17/17 |

FOREIGN PATENT DOCUMENTS

| | | |
|---|---|---|
| EP | 2962650 A1 | 1/2016 |
| JP | 2019521776 A | 8/2019 |
| WO | WO-2015106136 A1 | 7/2015 |
| WO | 2018009780 | 1/2018 |

OTHER PUBLICATIONS

"Australian Application Serial No. 2017293923, Response filed Aug. 13, 2019 to First Examination Report dated Apr. 10, 2019", 19 pgs.

"International Application Serial No. PCT/US2017/041077, Invitation to Pay Add'l Fees and Partial Search Rpt dated Sep. 27, 2017", 11 pgs.

"European Application Serial No. 17740864.8, Response to Communication pursuant to Rules 161(1) and 162 EPC filed Sep. 16, 2019", 19 pgs.

"International Application Serial No. PCT/US2017/041077, International Search Report dated Nov. 20, 2017", 6 pgs.

"International Application Serial No. PCT/US2017/041077, Written Opinion dated Nov. 20, 2017", 11 pgs.

"Canadian Application Serial No. 3,030,139, Office Action dated Nov. 26, 2019", 4 pgs.

"International Application Serial No. PCT US2017 041077, International Preliminary Report on Patentability dated Jan. 17, 2019", 11 pgs.

"Japanese Application Serial No. 2019-500376, Notification of Reasons for Rejection dated Feb. 4, 2020", with English translation, 7 pages.

"Canadian Application Serial No. 3,030,139, Response filed Mar. 26, 2030 to Office Action dated Nov. 26, 2019", 20 pgs.

* cited by examiner

REAMER AND GUIDE FOR GLENOID AUGMENT PREPARATION

CROSS-REFERENCE TO RELATED APPLICATION

The present application claims priority to U.S. Provisional Patent Application No. 62/374,222 filed on Aug. 12, 2016 and U.S. Provisional Patent Application No. 62/360,127, filed on Jul. 8, 2016, the contents of which are hereby incorporated in their entirety.

FIELD OF THE DISCLOSURE

The present disclosure relates to surgical instruments and methods for performing shoulder arthroplasty including a hemi shoulder arthroplasty and a total shoulder arthroplasty.

BACKGROUND

In a healthy shoulder, the proximal humerus is generally ball-shaped, and articulates within a socket, called the glenoid, formed by the scapula to form the shoulder joint. Conventional implant systems for the total replacement of the shoulder joint due to disease or trauma, i.e., a total shoulder arthroplasty, generally replicate the natural anatomy of the shoulder, and typically include a humeral component having a stem which fits within the humeral canal, and an articulating head which articulates within the socket of a glenoid component implanted within the glenoid of the scapula. An implant system for the replacement of only the humeral component of the shoulder joint, i.e., a hemi shoulder arthroplasty, typically includes only a humeral component which articulates within the natural glenoid socket of the scapula.

In addition, "reverse" type implant systems have been developed in which the conventional ball-and-socket configuration that replicates the natural anatomy of the shoulder is reversed, such that a concave recessed articulating component is provided at the proximal end of the humeral component that articulates against a convex portion of the glenoid component. Such reverse shoulder implant systems are thought to provide an increased range of motion for treatment of glenohumeral arthritis associated with irreparable rotator cuff damage, for example, by moving the center of rotation between the humeral component and the glenoid component to allow the deltoid muscles to exert a greater lever arm on the humerus.

SUMMARY

To better illustrate the reaming apparatus disclosed herein, a non-limiting list of examples is provided here:

In Example 1, a reaming apparatus can comprise a base guide, a reamer, a reamer driver, and a guide shaft. The base guide can define a base guide through bore, a base guide locking member, and a base guide articulating surface. The base guide articulating surface can be oriented at an angle relative to the base guide through bore. The reamer can define a reamer through bore and can include a first surface that can define a reamer gear and a second surface that can define a plurality of reamer teeth and a reamer articulating surface operable to allow rotation of the reamer on the base guide articulating surface. The reamer driver can define a reamer driver through bore and a reamer driver gear. The reamer driver gear can be sized to mesh with the reamer gear. The guide shaft can define a reamer driver receiver and a guide shaft locking member. The guide shaft locking member can be operable to engage the base guide locking member thereby securing the guide shaft to the base guide. Upon assembly of the reaming apparatus the base guide through bore, the reamer through bore, and the reamer driver through bore can be coaxial.

In Example 2, the reaming apparatus of Example 1 can optionally be configured such that the angle that the base guide through bore is oriented relative to the base guide articulating surface can be non-orthogonal.

In Example 3, the reaming apparatus of any one or any combination of Examples 1 and 2 can optionally be configured such that the first surface includes a recessed portion and a sidewall. The reamer gear can be defined by the sidewall.

In Example 4, the reaming apparatus of any one or any combination of Examples 1-3 can optionally be configured such that the reamer gear can be defined at an angle relative to the reamer articulating surface.

In Example 5, the reaming apparatus of any one or any combination of Examples 1-4 can optionally be configured such that the base guide further defines a boss. The reamer through bore can be sized to allow at least a portion of the boss to pass into the reamer through bore.

In Example 6, the reaming apparatus of any one or any combination of Examples 1-5 can optionally be configured such that the reamer driver gear and the reamer gear form an epicyclic gear train.

In Example 7, the reaming apparatus of any one or any combination of Examples 1-6 can optionally be configured such that the reamer gear and the reamer driver gear each include a plurality of complementary surfaces. The complementary surfaces can be configured to act together to form a geared system.

In Example 8, the reaming apparatus of any one or any combination of Examples 1-7 can optionally be configured such that the base guide locking member defines a locking peg.

In Example 9, the reaming apparatus of any one or any combination of Examples 1-8 can optionally be configured such that the guide shaft locking member defines an opening.

In Example 10, the reaming apparatus of any one or any combination of Examples 1-9 can optionally be configured to further include a guide rod. The guide rod can be configured to be connected to a glenoid and sized to receive the base guide through bore, the reamer through bore, and the reamer driver through bore.

In Example 11, the reaming apparatus of any one or any combination of Examples 1-10 can optionally be configured such that the base guide further includes an alignment peg.

In Example 12, a reaming system can include a plurality of base guides, a reamer, a reamer driver, and a guide shaft. Each of the plurality of base guides can define a base guide through bore, a base guide locking member, and a base guide articulating surface. The base guide articulating surface of each of the plurality of base guides can be oriented at an angle relative to the base guide through bore. The angle the base guide articulating surface is oriented relative to the base guide through bore can be different for each of the plurality of base guides. The reamer can define a reamer through bore and can include a first surface that can define a reamer gear and a second surface that can define a plurality of reamer teeth. A reamer articulating surface can be operable to allow rotation of the reamer on the base guide articulating surface. The reamer driver can define a reamer driver through bore and a reamer driver gear. The reamer driver gear can be sized to mesh with the reamer gear. The guide shaft can define a reamer driver receiver and a guide shaft locking member. The guide shaft locking member can be operable to engage the base guide locking member thereby securing the guide shaft to the base guide. Upon assembly of a reaming apparatus the base guide through bore of one of the plurality of base guides, the reamer through bore, and the reamer driver through bore can be coaxial.

In Example 13, the reaming system of Example 12 can optionally be configured such that the angle the base guide articulating surface is oriented relative to the base guide through bore for each of the plurality of base guides can be non-orthogonal.

In Example 14, the reaming system of any one or any combination of Examples 12 and 13 can optionally be configured such that the second surface includes a recessed portion and a sidewall. The reamer gear can be defined by the sidewall.

In Example 15, the reaming system of any one or any combination of Examples 12-14 can optionally be configured such that the reamer gear can be defined at an angle relative to the reamer articulating surface.

In Example 16, the reaming system of any one or any combination of Examples 12-15 can optionally be configured such that the reamer driver gear and the reamer gear form an epicyclic gear train when the reaming apparatus is assembled.

In Example 17, the reaming system of any one or any combination of Examples 12-16 can optionally be configured such that the base guide locking member defines a locking peg.

In Example 18, the reaming system of any one or any combination of Examples 12-17 can optionally be configured such that the guide shaft locking member defines an opening.

In Example 19, the reaming system of any one or any combination of Examples 12-18 can optionally include a guide rod. The guide rod can optionally be configured to connect to a glenoid and sized to receive the base guide through bore, the reamer through bore, and the reamer driver through bore.

In Example 20, the reaming system of any one or any combination of Examples 12-19 can optionally be configured such that each of the plurality of base guides further includes an alignment peg.

In Example 21, a method for reaming a glenoid can include forming an incision in a patient to expose the glenoid; attaching a central wire to a central axis of the glenoid; assembling a reaming apparatus; sliding a portion of the reaming apparatus along the central wire and through the incision; and reaming the glenoid using the reaming apparatus. Assembling the reaming apparatus can include aligning central bores for two or more components of the reaming apparatus such that each is coaxial.

In Example 22, the method of Example 21 can optionally include drilling a hole in the glenoid. The hole can be for a peripheral alignment peg of the reaming apparatus.

In Example 23, the method of any one or any combination of Examples 21 and 22 reaming the glenoid can optionally include reaming the glenoid until at least 50% of a glenoid face has been prepared.

In Example 24, the method of any one or any combination of Examples 21-23 can optionally include the central wire being collinear with the central axis.

In Example 25, the method of any of Examples 21-24 can optionally selecting a base guide for the reaming apparatus from a plurality of base guides. Each of the plurality of base guides can be configured to orient a reamer at a different angle relative to the central wire.

Example 26 includes a reaming apparatus. The reaming apparatus can include a base guide, a reamer, and a reamer driver. The base guide can include a base guide through bore, a base guide articulating surface, and a base peg. The base guide through bore can have a bore axis. The base peg can have a peg axis. The base guide articulating surface can be oriented perpendicular to the bore axis. The peg axis can be oriented at an angle relative to the bore axis. The reamer can define a reamer socket and a reamer articulation surface. The reamer can include a reamer peg and a plurality of cutting arms. The reamer peg can be sized to be received in the base guide through bore and can extend from the reamer articulation surface. The plurality of cutting arms can be arranged perpendicular to the reamer peg. The reamer driver can define a reamer drive ball configured to be received in the reamer socket and upon rotation of the reamer driver, cause the reamer to rotate.

In Example 27, the reaming apparatus of Example 26 can optionally include the reamer socket and the reamer drive ball each including a plurality of complementary surfaces. The complementary surfaces can be configured to act together to allow torque and rotation to be transmitted from the reamer driver to the reamer.

In Example 28, the reaming apparatus of any one of or any combination of Examples 26 and 27 can optionally include the base guide comprising an alignment peg offset from the base peg and oriented parallel to the base beg.

In Example 29, the reaming apparatus of any one of or any combination of Examples 26-28 can optionally include the base peg including a plurality of fins that project from an exterior surface of the base peg.

In Example 30, the reaming apparatus of any one of or any combination of Examples 26-29 can optionally include the base peg has a stepped profile.

In Example 31, the offset guide, systems, or methods of any one of or any combination of Examples 1-30 are optionally configured such that all elements or options recited are available to use or select from.

BRIEF DESCRIPTION OF THE FIGURES

The above-mentioned and other features and advantages of this invention, and the manner of attaining them, will become more apparent and the invention itself will be better understood by reference to the following description of examples of the invention taken in conjunction with the accompanying drawings, wherein.

Corresponding reference characters indicate corresponding parts throughout the several views. The exemplifications set out herein illustrate examples of the invention, and such exemplifications are not to be construed as limiting the scope of the invention any manner.

DETAILED DESCRIPTION

Figure 1:
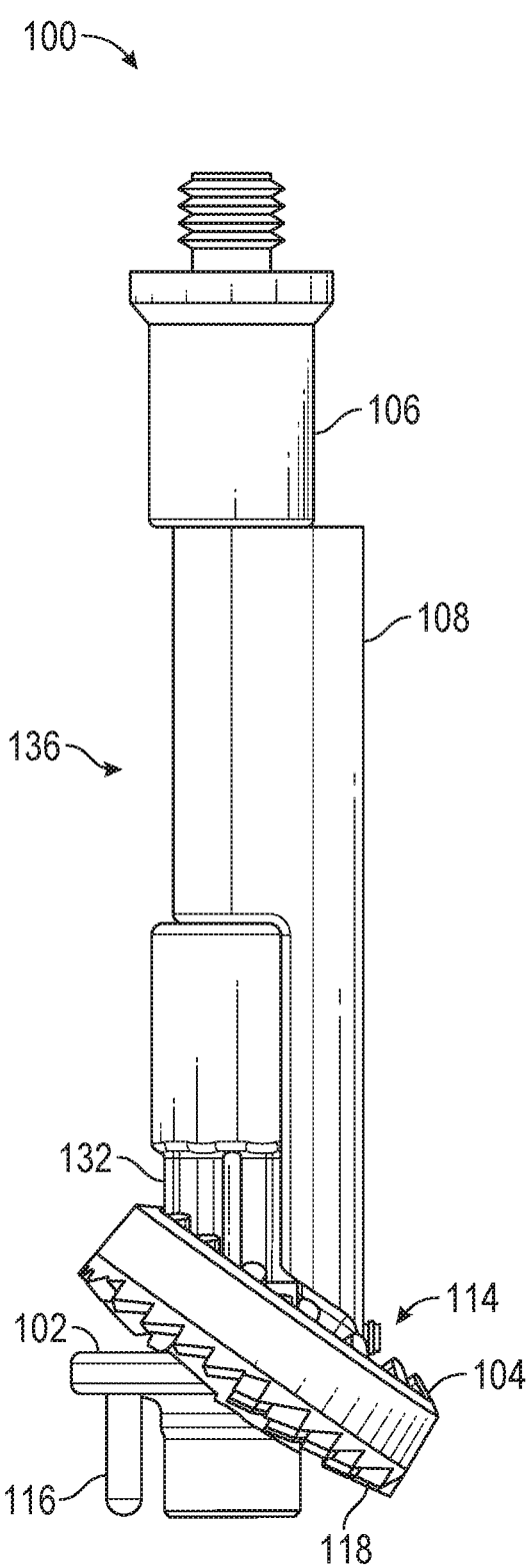
FIG. 1 shows a side view of a reaming apparatus in accordance with at least one example of the present disclosure.
Figure 2:
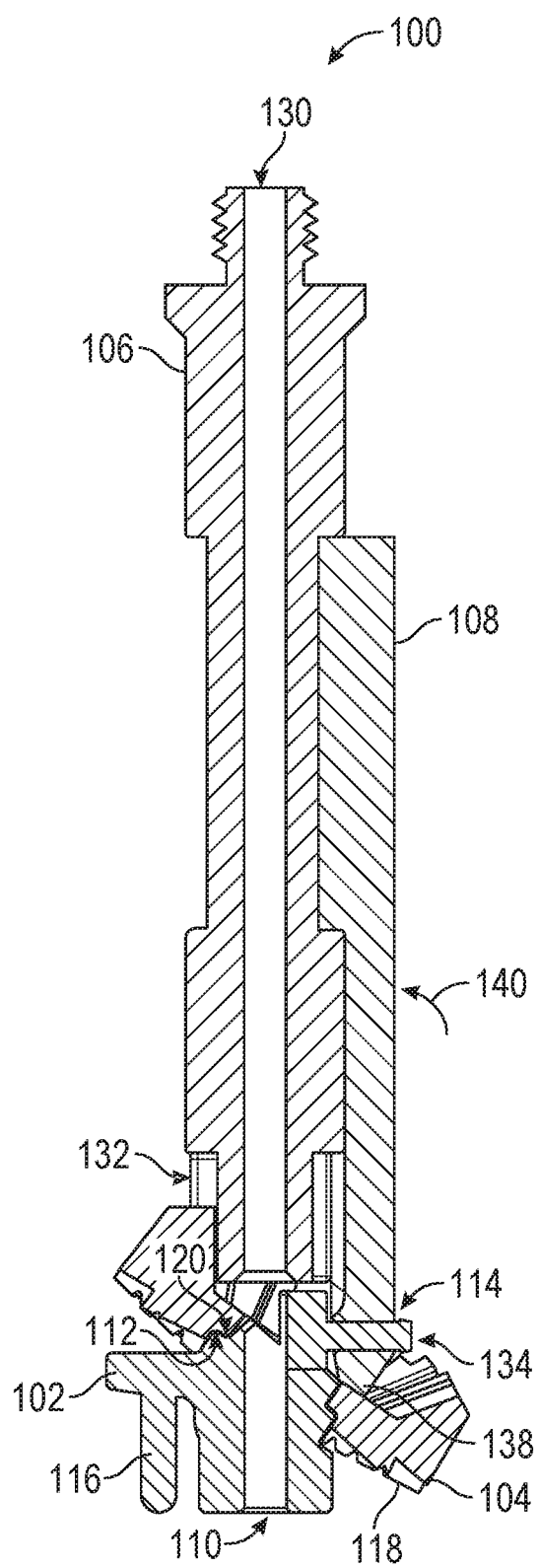
FIG. 2 shows a section view of a reaming apparatus in accordance with at least one example of the present disclosure.

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves.

Preparation of glenoid bone for augmented glenoid components used in shoulder arthroplasty (anatomic and reverse) can involve a complicated preparation method. Exposure limitations and a tight joint space can restrict access to the glenoid face. When a preparation procedure requires a surgeon to approach the glenoid from an off-axis angle, the surgeon can be forced to fight exposure limitations. This can be even more so when approaching the glenoid from the posterior side.

In view of exposure limitations and to increase ease of access to the glenoid, the various components of a reaming apparatus can be preassembled prior to inserting the reaming apparatus into the body. For example, a reaming apparatus can include a base guide, a reamer, and a reamer driver gear. The base guide, reamer, and reamer driver gear can be assembled by a surgeon or surgical technician prior to beginning a shoulder arthroplasty. Once the joint capsule and glenoid have been accessed, the reaming apparatus can be inserted into the body via the incision.

By assembling the reaming apparatus outside the body, the surgical time can be decreased. Decreased surgical time can have many advantages such as, but not limited to, decreased risk of infections, decreased surgeon fatigue, lower cost due to less time spent in an operating room, and decreased time under general anesthesia.

Referring now to the figures, FIGS. 1-4 show a reaming apparatus 100 consistent with examples disclosed herein. The reaming apparatus 100 can include a base guide 102, a reamer 104, a reamer driver 106, and a guide shaft 108. The base guide 102 can define a base guide through bore 110, a base guide articulating surface 112, a base guide locking member 114, and an alignment peg 116.

The base guide 102 can be constructed of a metal, a polymer, a ceramic, or any combination thereof. In addition, the base guide 102 can be manufactured using techniques such as, but not limited to, CNC machining, forging, casting, injection molding, additive manufacturing, and the like. The various surfaces of the base guide 102 can be finished with techniques such as, but not limited to, bead blasting, annealing, machining, etc. The surface finish of the base guide 102 can vary depending on needs of a particular patient. For example, a patient with extensive tissue damage or delicate tissue can need the base guide 102 to have a smoother surface finish to minimize further tissue damage.

The reamer 104 can define a plurality of teeth 118 and a reamer articulation surface 120. The reamer 104 can also include a sidewall 122 and a recessed portion 124. The sidewall 122 can define a reamer gear 126 having a plurality of teeth. The sidewall 122 can be at an angle relative to a central reamer bore 142 that passes through the reamer 104. The reamer gear 126 can be defined at an angle to the reamer articulation surface 120. Having the reamer gear 126 defined at an angle can allow the reamer 104 to be positioned at an angle relative the guide shaft 108 as discussed herein.

The base guide articulation surface 112 can define a boss 144 and the through the central reamer bore 142 can allow the boss 144, or a portion of the boss 144, to pass through the reamer 104 such that the reamer articulation surface 120 rests on the base guide articulation surface 112. The boss 144 can then act as an axle about which the reamer 104 can rotate.

The reamer 104 can be constructed of a metal, a polymer, a ceramic, or any combination thereof. For example, the reamer 104 can be a multicomponent piece and the plurality of teeth 118 can be fashioned out of metal while the sidewall 122 and reamer gear 126 can be fashioned out of a polymer. In addition, the reamer 104 can be manufactured using techniques such as, but not limited to, CNC machining, forging, casting, injection molding, etc. The various surfaces of the reamer 104 can be finished with techniques such as, but not limited to, bead blasting, annealing, machining, etc. The surface finish of the reamer 104 can vary depending on needs of a particular patient. For example, a patient with extensive tissue damage or delicate tissue can need an outer surface 128 of the reamer 104 to have a smoother surface finish to minimize further tissue damage.

The reamer driver 106 can define a reamer driver through bore 130 and a reamer driver gear 132. The reamer driver gear 132 can be defined as a plurality of teeth that can engage the teeth defined by the sidewall 122 of the reamer 104. The reamer driver gear 132 can also include a plurality of surfaces 502 (see FIG. 5) that engage complementary surfaces in a reamer drive socket 504 (see FIG. 5). During use, the reamer drive gear 132 can interact with the reamer 104 such that rotation of the reamer driver 106 causes the reamer to rotate about a central axis of the reaming apparatus 100. Stated another way, in various examples, the reamer driver gear 132 and reamer gear 126 can form an epicyclic gear train.

Figure 5:
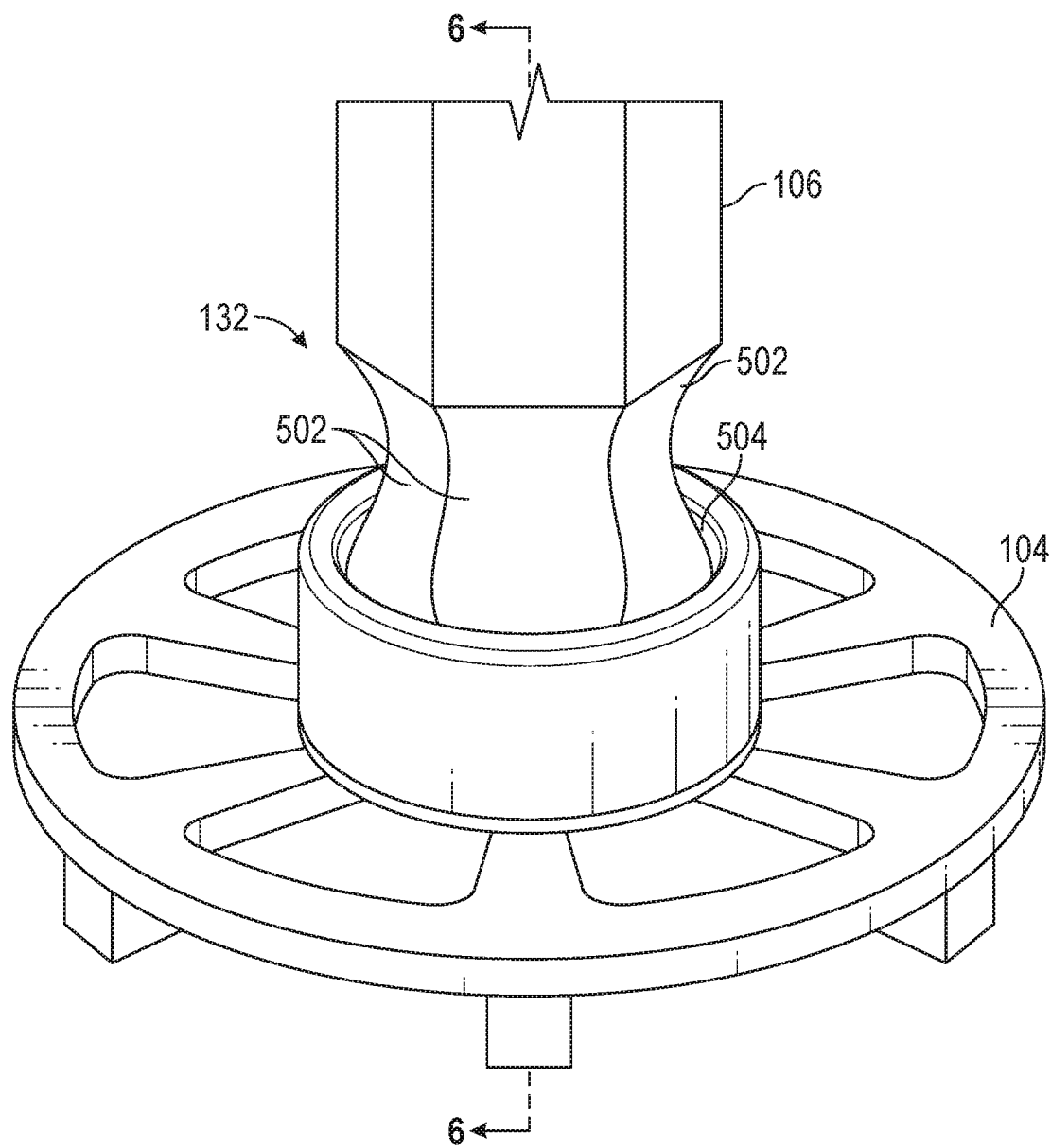
FIG. 5 shows reamer drive gear components and reamer components of a reaming apparatus in accordance with at least one example of the present disclosure.
Figure 6:
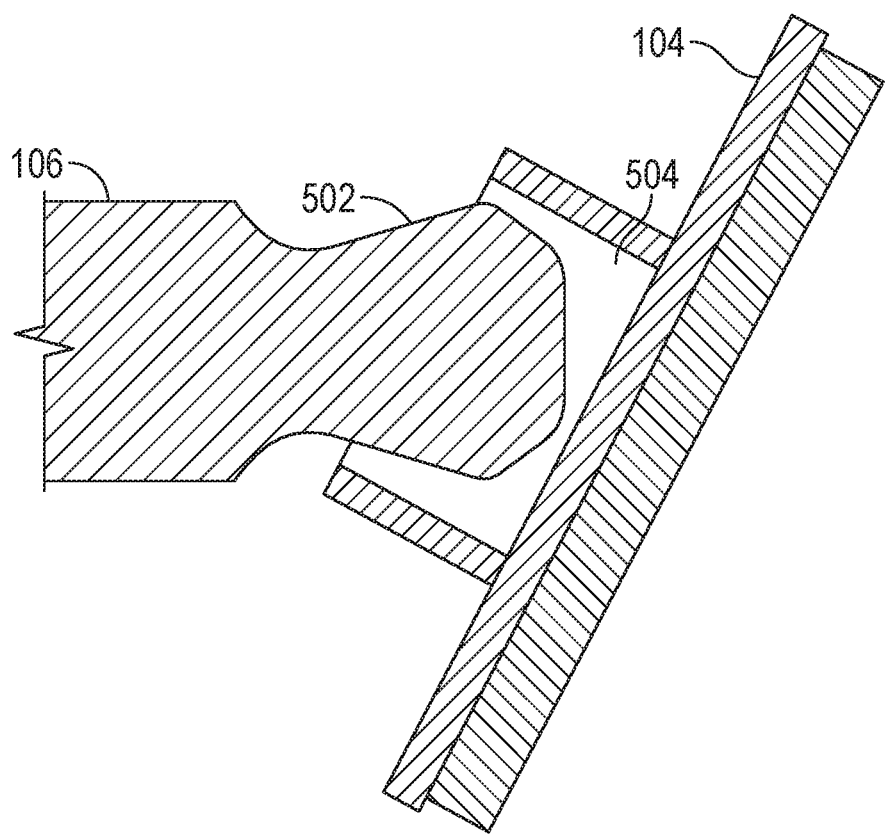
FIG. 6 shows a section view of reamer drive gear components and reamer components of a reaming apparatus in accordance with at least one example of the present disclosure.

In addition, the reamer driver gear 132 and the reamer gear 126 can have teeth with planar or curved surfaces. For example, as shown in FIGS. 1-4, the various teeth of the reamer driver gear 132 and the reamer gear 126 can have straight, or planar, surfaces that form a beveled gear system. In addition, as shown in FIGS. 5 and 6, the surfaces 502 and the reamer drive socket 504 can have curved surfaces that mesh and form a geared system.

The reamer driver 106 can be constructed of a metal, a polymer, a ceramic, or any combination thereof. For example, the reamer driver 106 can be a multicomponent piece and the reamer driver gear 132 can be fashioned out of metal while the remainder of the reamer driver 106 can be fashioned out of a polymer. In addition, the reamer driver 106 can be manufactured using techniques such as, but not limited to, CNC machining, forging, casting, injection molding, etc. The various surfaces of the reamer driver 106 can be finished with techniques such as, but not limited to, bead blasting, annealing, machining, etc. The surface finish of the various surfaces of the reamer driver 106 can vary from one another. For example, the surface of the reamer driver 106 that contacts the guide shaft 108 can be polished to reduce friction while the other surfaces of the reamer driver 106 have a non-polished finish.

Figure 3:
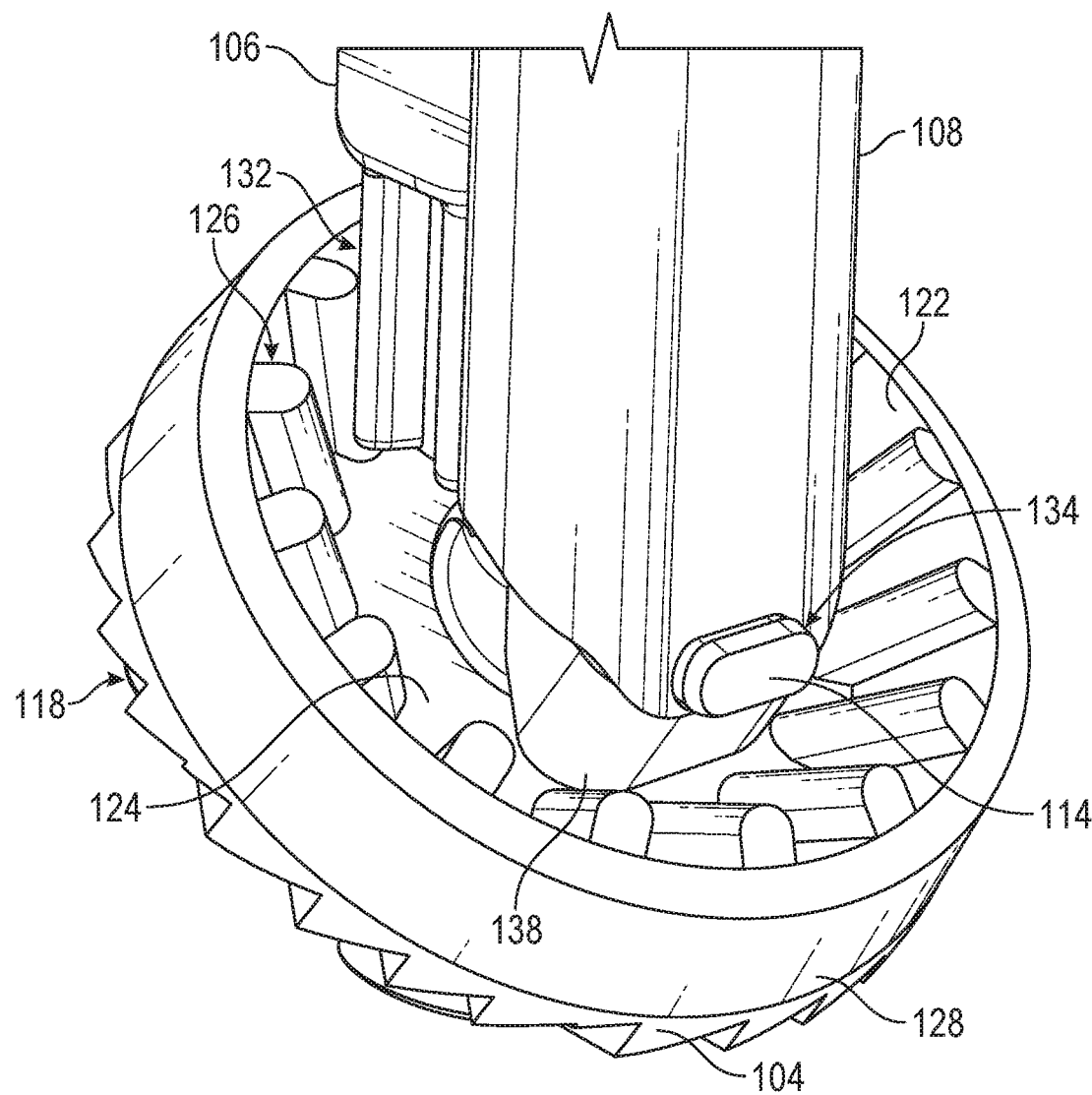
FIG. 3 shows a perspective view of a portion of a reaming apparatus in accordance with at least one example of the present disclosure.
Figure 4:
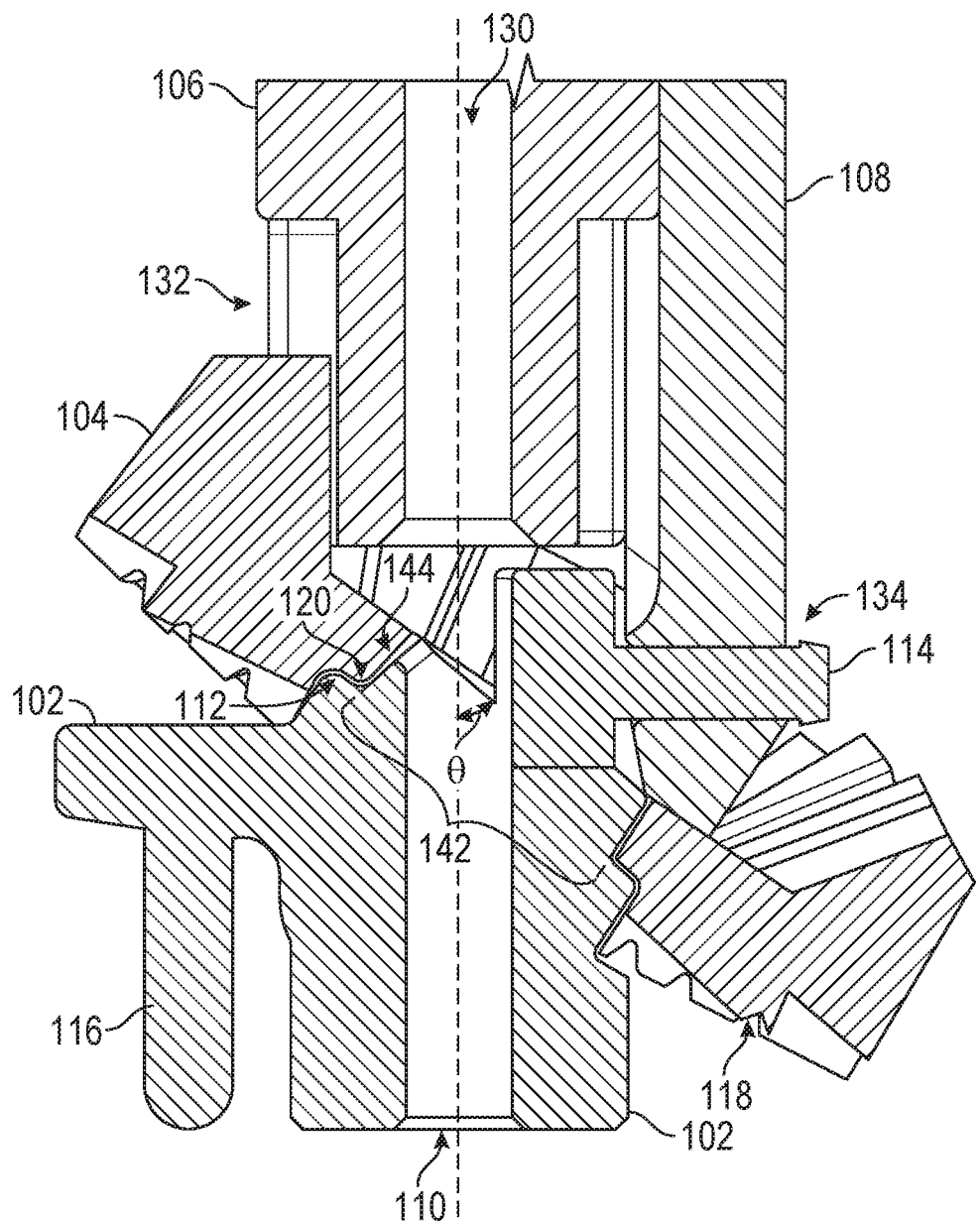
FIG. 4 shows a section view of a portion of a reaming apparatus in accordance with at least one example of the present disclosure.

The guide shaft 108 can define a guide shaft locking member 134 and a reamer driver receiver 136. The guide shaft locking member 134 can operate with the base guide locking member 114 to secure the base guide 102 to the guide shaft 108. For example, as shown in FIG. 3, a portion 138 of the guide shaft 108 can be located proximate sidewall 122 or reamer gear 136. Once the portion 138 is in position, the guide shaft 108 can be tilted, as indicated by arrow 140 such that the base guide 114, which can be fashioned in the shape of a peg with barbs, can pass through the guide shaft locking member 134. The barbs can secure the base guide locking member 114 to the to the guide shaft 108.

During tilting of the guide shaft 108 as indicated by arrow 140, the reamer driver 106 can be received into the reamer driver receiver 136. For example, the guide shaft can be formed of a polymer and the sidewalls of the guide shaft 108 that define the reamer driver receiver 136 can be flexible. As the reamer driver 106 is pressed into the reamer driver receiver, the sidewalls of the guide shaft 108 can flex and allow the reamer driver 106 to pass into a cavity defined by the guide shaft 108. The sidewalls of the guide shaft 108 that define the reamer driver receiver can curve partially around the reamer driver 106 thereby securing the reamer driver 106 into the reamer driver receiver 136.

The guide shaft 108 can be constructed of a metal, a polymer, a ceramic, or any combination thereof. In addition, the guide shaft 108 can be a multicomponent piece. For example, a portion of the guide shaft 108 can be fashioned out of metal and another portion of the guide shaft 108 can be fashioned out of a polymer. The guide shaft 108 can be manufactured using techniques such as, but not limited to, CNC machining, forging, casting, injection molding, etc. The various surfaces of the guide shaft 108 can be finished with techniques such as, but not limited to, bead blasting, annealing, machining, etc. The surface finish of the various surfaces of the guide shaft 108 can vary from one another. For example, the surface of the guide shaft 108 that contacts the reamer driver 106 can be polished to reduce friction while the other surfaces of the guide shaft 108 have a non-polished finish.

As shown in FIG. 1, the reamer 104 can be oriented at an angle relative to the base guide through bore 110. The orientation angle, θ, can be defined by an angle of the base guide articulating surface 112 relative to the base guide through bore 110. In addition, the reaming apparatus 100 can be part of a system that includes multiple base guides 102. Each of the base guides 102 can have a base guide articulating surface 112 that is orientated at a non-orthogonal angle to the base guide through bore 110. For example, the system can include three base guides 102. The three base guides 102 can have orientation angles of 10°, 20°, and 30°, respectively.

Figure 7:
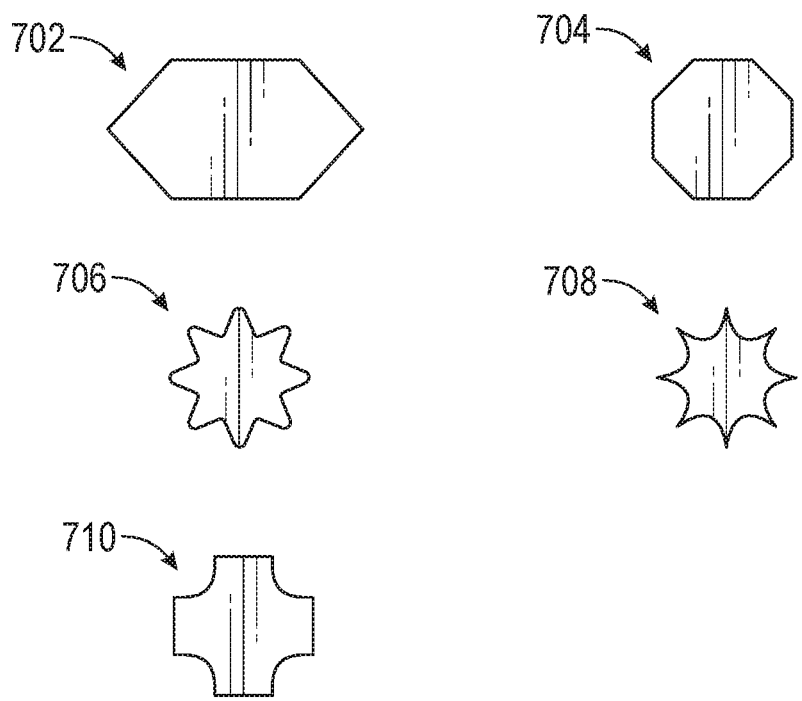
FIG. 7 shows various profiles for reamer drive gears in accordance with various examples of the present disclosure.

As shown and briefly discussed above, FIGS. 5 and 6 show the reamer driver 106 having surfaces 502 that interact with complementary surfaces of the reamer socket 504 of the reamer 104. As shown in FIG. 7, the surfaces 502 can vary in number and in shape. FIG. 7 shows varying profiles for the reamer driver 106. Profile 702 shows the surfaces 502 number six and profile 704 shows the surfaces 502 number eight. The number of surfaces 502 can be an even number or an odd number. For example, the number of surfaces can range from 6-20, or more. In addition, the profile formed by the surfaces 502 can be regular or irregular. For example, the profile can be a regular octagon or an irregular octagon. Furthermore, as shown by profiles 706 and 708, the surfaces 502 can be curved. In addition, as shown in profile 710, the surfaces 502 can be a combination of planar and curved surfaces.

During a shoulder replacement, a surgeon can form an incision in a patient to expose the glenoid. Once the glenoid is exposed the surgeon can attach a central wire to a central axis of the glenoid. While, or before, the surgeon begins making the incision and exposing the glenoid, the surgeon, or a technician, can assemble the reamer device 100. During the assembly of the reamer device 100, the reamer driver through bore 130 and the base guide through bore 110 can be aligned such that they are coaxial. A bore in the reamer 104 can be aligned at an angle to the central axis. During the assembly, the base guide 102 having an appropriate angle of orientation can be selected.

Once the reamer device 100 is assembled, the reamer device 100 can be slide along the central wire by passing the central wire through the coaxial bores. The reamer device 100 can be slid such that the base guide 102 and the reamer 104 pass through the incision and contact the glenoid. In addition, the surgeon can drill a hole in the glenoid. The drilled hole can receive the alignment peg 116. Once the reamer device 100 is in position, the glenoid can be reamed as necessary. For example, the glenoid can be reamed until at least 50% of the glenoid face has been prepared.

Figure 8:
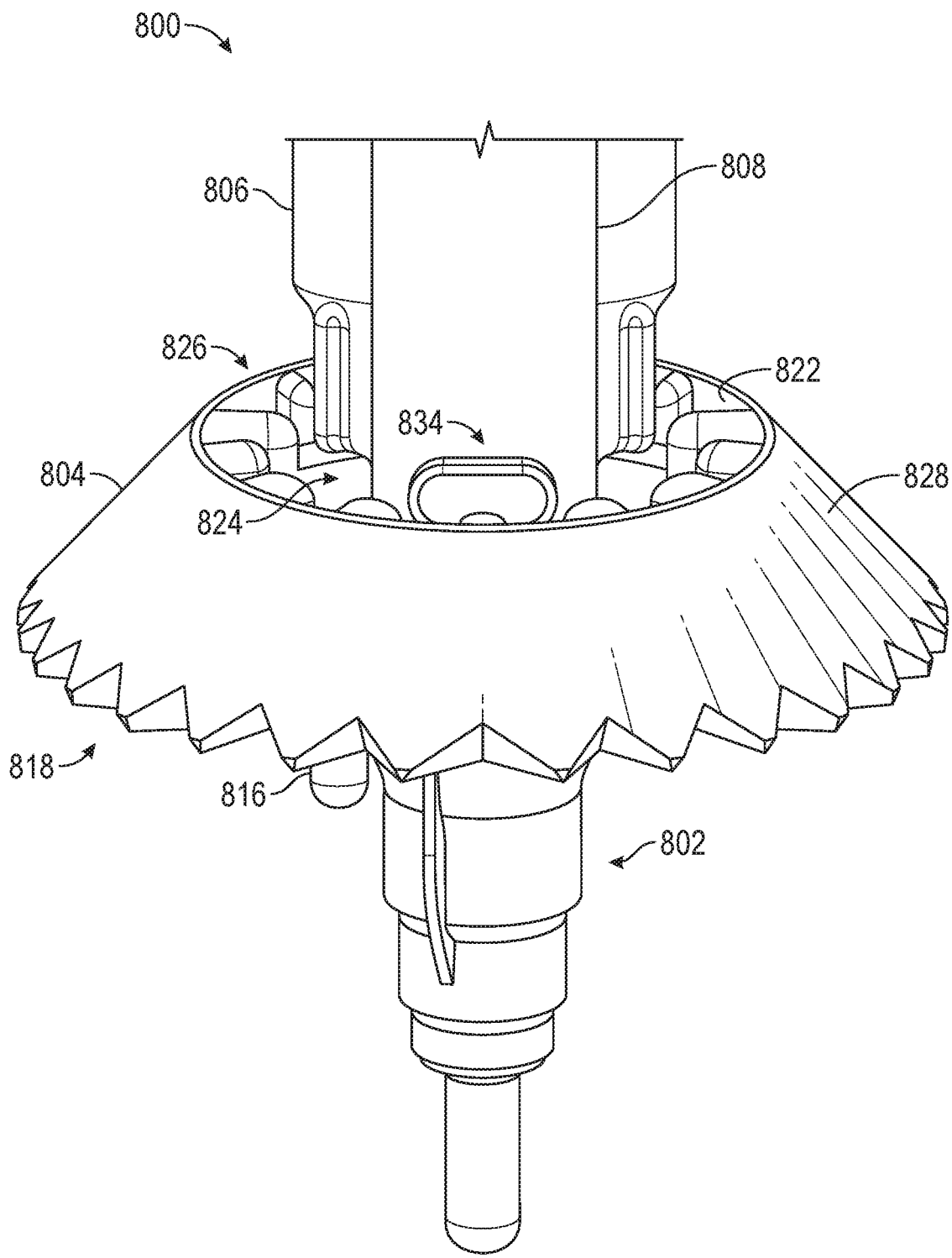
FIG. 8 shows reamer drive gear components and reamer components of a reaming apparatus in accordance with at least one example of the present disclosure.

FIG. 8 shows reamer drive gear components and reamer components of a reaming apparatus 800 in accordance with at least one example of the present disclosure. The reaming apparatus 800 can include a base guide 802, a reamer 804, a reamer driver 806, and a guide shaft 808. The base guide 802 can define a base guide locking member 814 and an alignment peg 816. Other features such as those described above with respect to FIGS. 1-4 can also be defined by the base guide locking member 814.

The base guide 802 can be constructed of a metal, a polymer, a ceramic, or any combination thereof. In addition, the base guide 802 can be manufactured using techniques such as, but not limited to, CNC machining, forging, casting, injection molding, etc. The various surfaces of the base guide 802 can be finished with techniques such as, but not limited to, bead blasting, annealing, machining, etc. The surface finish of the base guide 802 can vary depending on needs of a particular patient. For example, a patient with extensive tissue damage or delicate tissue may need the base guide 802 to have a smoother surface finish to minimize further tissue damage.

The reamer 804 can define a plurality of teeth 818. The reamer 804 can also include a sidewall 822 and a recessed portion 824. The sidewall 822 can define a reamer gear 826 having the plurality of teeth. The sidewall 822 can be at an angle relative to a central reamer bore that passes through the reamer 804. The reamer gear 826 can be defined at an angle to the reamer articulation surface. Having the reamer gear 826 defined at an angle can allow the reamer 804 to be positioned at an angle relative the guide shaft 808 as discussed herein.

The reamer 804 can be constructed of a metal, a polymer, a ceramic, or any combination thereof. For example, the reamer 804 can be a multicomponent piece and the plurality of teeth 818 can be fashioned out of metal while the sidewall 822 and reamer gear 826 can be fashioned out of a polymer. In addition, the reamer 804 can be manufactured using techniques such as, but not limited to, CNC machining, forging, casting, injection molding, etc. The various surfaces of the reamer 804 can be finished with techniques such as, but not limited to, bead blasting, annealing, machining, etc. The surface finish of the reamer 804 can vary depending on needs of a particular patient. For example, a patient with extensive tissue damage or delicate tissue can need an outer surface 828 of the reamer 804 to have a smoother surface finish to minimize further tissue damage.

The reamer driver 806 can define a reamer driver gear 832. The reamer driver gear 832 can be defined as a plurality of teeth that can engage the teeth defined by the sidewall 822 of the reamer 804. During use, the reamer drive gear 832 can interact with the reamer 804 such that rotation of the reamer driver 806 causes the reamer to rotate about a central axis of the reaming apparatus 800. Stated another way, in various examples, the reamer driver gear 832 and reamer gear 826 can form an epicyclic gear train.

The reamer driver 806 can be constructed of a metal, a polymer, a ceramic, or any combination thereof. For example, the reamer driver 806 can be a multicomponent piece and the reamer driver gear 832 can be fashioned out of metal while the remainder of the reamer driver 806 can be fashioned out of a polymer. In addition, the reamer driver 806 can be manufactured using techniques such as, but not limited to, CNC machining, forging, casting, injection molding, etc. The various surfaces of the reamer driver 806 can be finished with techniques such as, but not limited to, bead blasting, annealing, machining, etc. The surface finish of the various surfaces of the reamer driver 806 can vary from one another. For example, the surface of the reamer driver 806 that contacts the guide shaft 808 can be polished to reduce friction while the other surfaces of the reamer driver 806 have a non-polished finish.

The guide shaft 808 can define a guide shaft locking member 834 and a reamer driver receiver 836. The guide shaft locking member 834 can operate with the base guide locking member 814 to secure the base guide 802 to the guide shaft 808. The guide shaft 808 can be constructed of a metal, a polymer, a ceramic, or any combination thereof. In addition, the guide shaft 808 can be a multicomponent piece. For example, a portion of the guide shaft 808 can be fashioned out of metal and another portion of the guide shaft 808 can be fashioned out of a polymer. The guide shaft 808 can be manufactured using techniques such as, but not limited to, CNC machining, forging, casting, injection molding, etc. The various surfaces of the guide shaft 808 can be finished with techniques such as, but not limited to, bead blasting, annealing, machining, etc. The surface finish of the various surfaces of the guide shaft 808 can vary from one another. For example, the surface of the guide shaft 808 that contacts the reamer driver 806 can be polished to reduce friction while the other surfaces of the guide shaft 808 have a non-polished finish.

As stated previously, when a preparation procedure requires a surgeon to approach the glenoid from an off-axis angle, the surgeon can be forced to fight exposure limitations. This can be even more so when approaching the glenoid from the posterior side.

In view of exposure limitations and to increase ease of access to the glenoid, the various components of the reaming apparatuses disclosed herein need not be preassembled prior to inserting the reaming apparatuses into the body. For example, a reaming apparatus can include a base guide, a reamer, and a reamer driver ball on a shaft. The base guide, reamer, and reamer driver ball shaft can be assembled easily by a surgeon in the wound, through whatever incision the patient's physiology allows. Once the joint capsule and glenoid have been accessed, the base guide can be inserted into the body via the incision as disclosed herein.

By assembling the reamer into the base guide, and then the reamer driver ball shaft into the reamer socket inside the incision, handling the components by other than the surgeon can be decreased. The chief advantage of this simplified reamer apparatus is the requirement for a large, complex coaxial mechanism is removed. There is no fixed coaxial relationship established between the reamer socket axis and the reamer driver ball shaft axis. This driving relationship will function anywhere within a cone of excursion of approximately 62°, enabling the surgeon to operate the reamer by placing the reamer drive ball shaft in the reamer socket while the shaft is also in the most advantageous place the wound access allows, within the approximately 62° cone.

Figure 9:
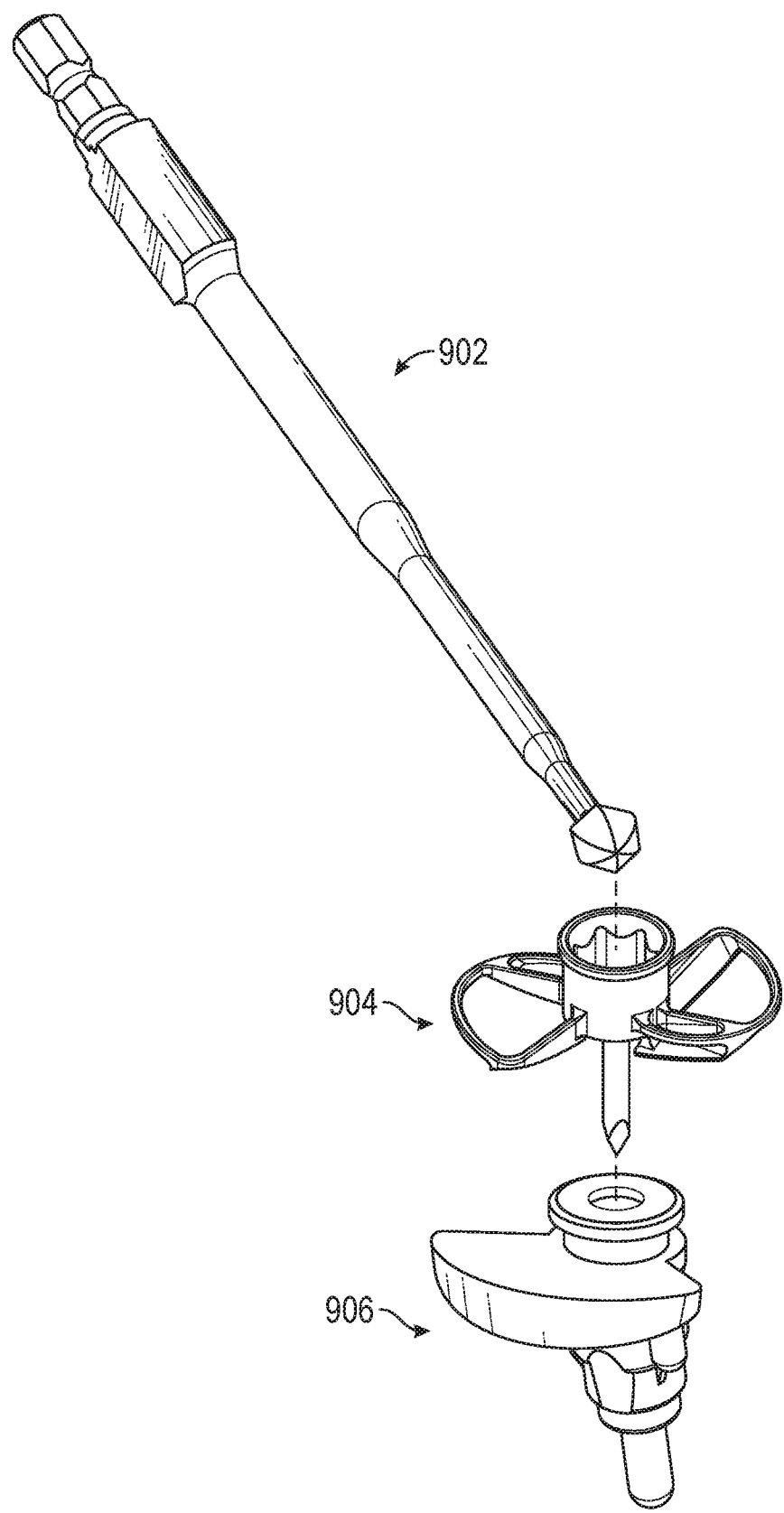
FIG. 9 shows a reaming apparatus in accordance with at least one example of the present disclosure.

FIG. 9 shows a reaming apparatus 900 in accordance with at least one example of the present disclosure. The reaming apparatus 900 can include a reamer driver 902, a reamer 904, and a base guide 906. During surgery, the base guide 906 can be temporarily implanted at the glenoid, or other bone. Once the base guide 906 is implanted, the reamer 904 can engage the base guide 906 as disclosed herein. Once the reamer 904 has engaged the base guide 906, the reamer driver 902 can be used to rotate the reamer 904 as disclosed herein.

Figure 10A:
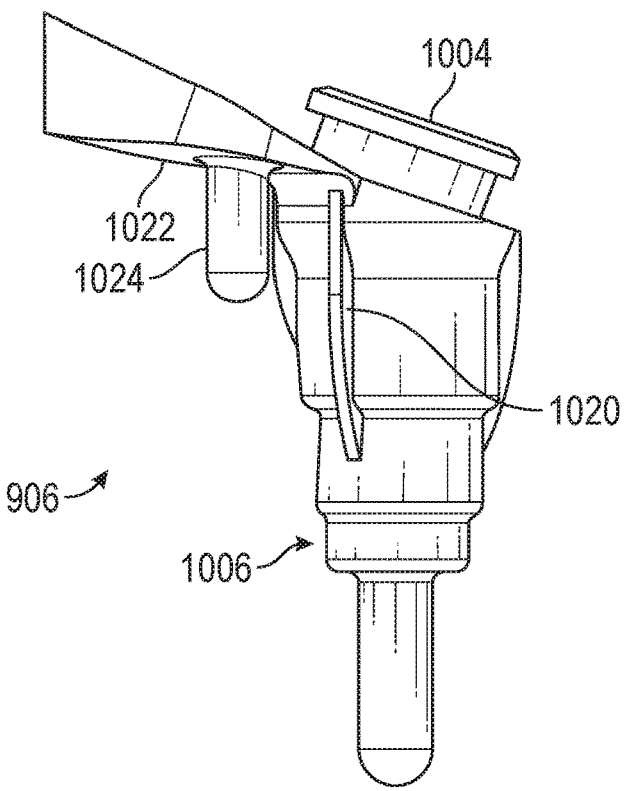
FIGS. 10A and 10B show a side view of a base guide and a section view of the base guide, respectively, in accordance with at least one example of the present disclosure.
Figure 10B:
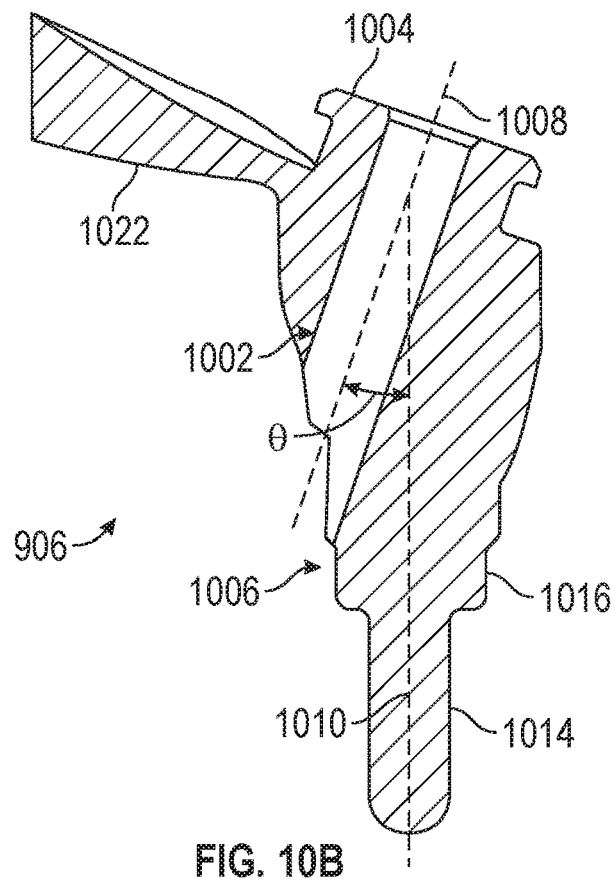

FIGS. 10A and 10B show a side view of the base guide 906 and a cross-section of the base guide 906. The base guide 906 can include a base guide through bore 1002, a base guide articulation surface 1004, and a base peg 1006. The base guide through bore 1002 can include a bore axis 1008. The base guide articulation surface 1004 can be oriented perpendicular to the bore axis 1008. The bore axis 1008 can be oriented at an angle, θ, to a peg axis 1010. The angle θ can allow a surgeon to access the glenoid at an angle or otherwise ream a surface of the glenoid at an angle such that a glenoid contacting surface of a glenoid component matches a contour of the reamed glenoid. The angle θ can range from about 5° to about 35°.

The base peg 1006 can have a stepped profile. For example, as shown in FIGS. 10A and 10B, the base peg 1006 can have a first section 1014 and a second section 1016. The first section 1014 can have a first diameter and the second section 1016 can have a second diameter. The first diameter can be less than the second diameter. The stepped profile can assist with implanting the base guide 906 by allowing for progressively smaller holes to be drilled into the glenoid, and thus reducing damage to the glenoid. In addition, base guide 906 can include one or more fins 1020. The fins 1020 can act to hinder rotation of the base guide 906 within bone and improve frictional engagement between the peg 100 and bone.

The base guide 906 can further include an extension 1022. The extension 1022 can be oriented perpendicular to the bore axis 1008. The underside of the extension 1022 (i.e., the portion proximate the glenoid when implanted) can have a curvature. The curvature can be concave, convex, or a combination of both. For example, a first portion of the underside of the extension 1022 can be concave to match a first contour of a first section of bone and second portion of the underside of the extension 1022 can be convex to match a second contour of a second portion of bone.

The extension 1022 can include an alignment peg 1024. The alignment peg 1024 can be offset from the base peg 1006. In addition, the alignment peg 1024 can be oriented parallel to the base peg 1006.

Figure 11A:
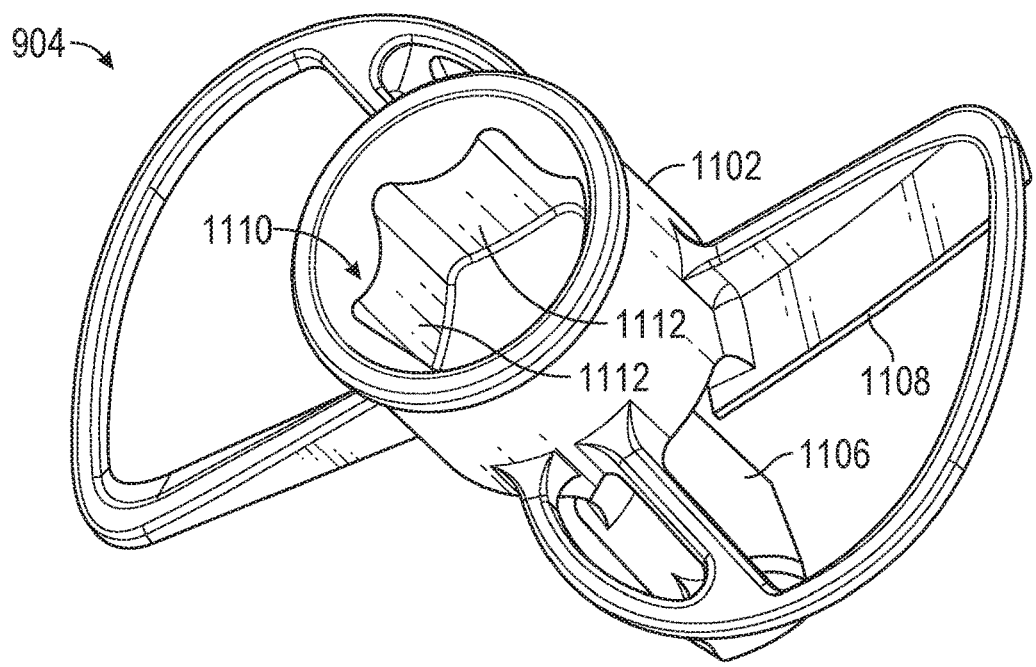
FIGS. 11A and 11B show perspective views of a reamer in accordance with at least one example of the present disclosure.
Figure 11B:
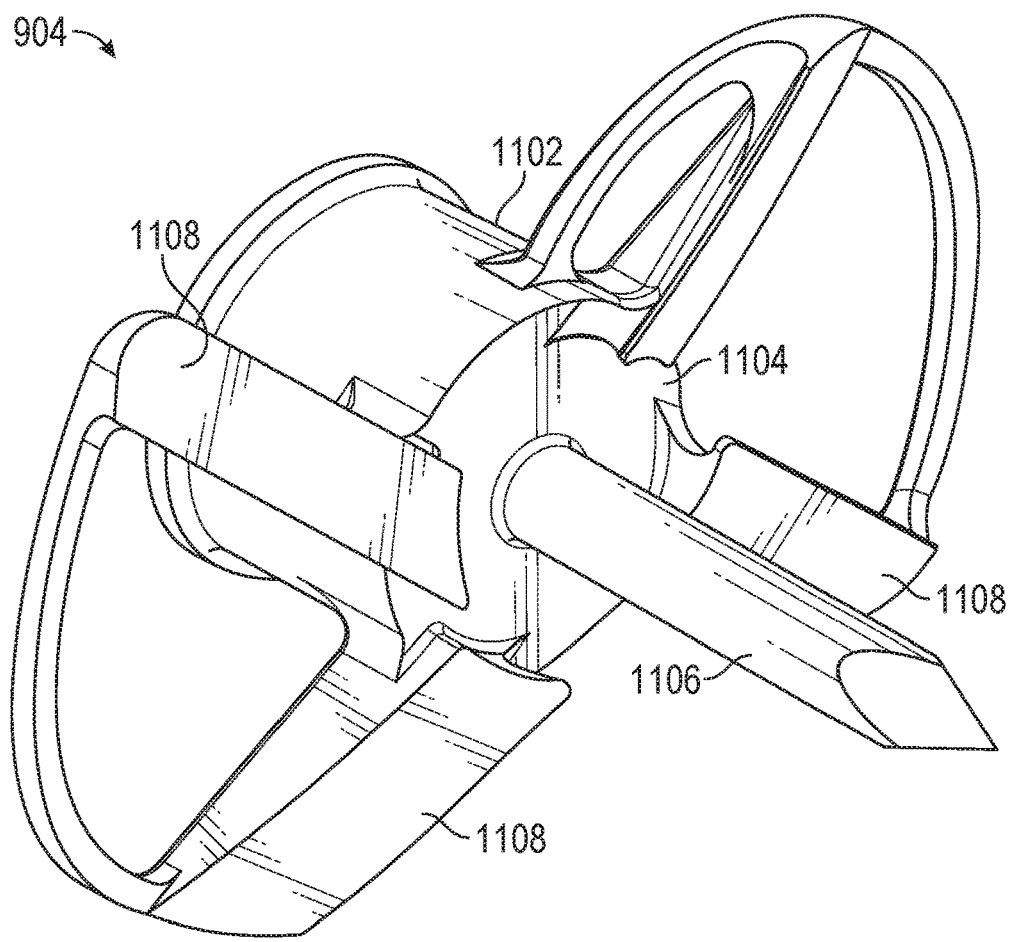

FIGS. 11A and 11B show top and bottom perspective views of the reamer 904. The reamer 904 can include a reamer body 1102. The reamer body 1102 can include an articulation surface 1104. The articulation surface 1104 can rest against a surface of the base guide 906 and allow for rotation of the reamer 904 in a stable position. A reamer peg 1106 can extend from the articulation surface 1104. The reamer peg 1106 can be sized to be received in the base guide through bore 1002 to facilitate rotation of the reamer 904 against the base guide 906 in a stable position.

The reamer 904 can also include cutting arms 1108. The cutting arms 1108 can extend from the reamer body 1102 and be parallel to the articulation surface 1104. The cutting arms 1108 can include sharp leading edges or a series of teeth that can cut tissue and bone. The cutting arms 1108 can be manufactured as a single piece or multiple pieces. For example, multiple teeth or other sharp instruments can be attached to form the cutting arms 1108. The cutting arms can also have a curvature to them. For example, the curvature can be concave, convex, or a combination of both. For example, a first portion of a cutting arm can be concave to ream a first contour into a first section of bone and second portion of the cutting arm can be convex to ream a second contour into a second portion of bone.

As shown in FIG. 11A, the reamer body 1102 can define a reamer socket 1110. The reamer socket 1110 can include reamer socket surfaces 1112. The reamer socket surfaces 1112 can cooperate with the reamer driver 902 as disclosed herein to cause the reamer 604 to rotate. In an example, the shape of the reamer socket 1110 can be hexagonal as shown in FIG. 11A. In another example, the reamer socket 1110 can be octagonal. However, any suitable shape (such as those described above with respect to FIGS. 5-7) that allows for the transmission of torque and rotation within the desired angle of excursion from the reamer driver 902 to the reamer body 1102 can be utilized.

Figure 12:
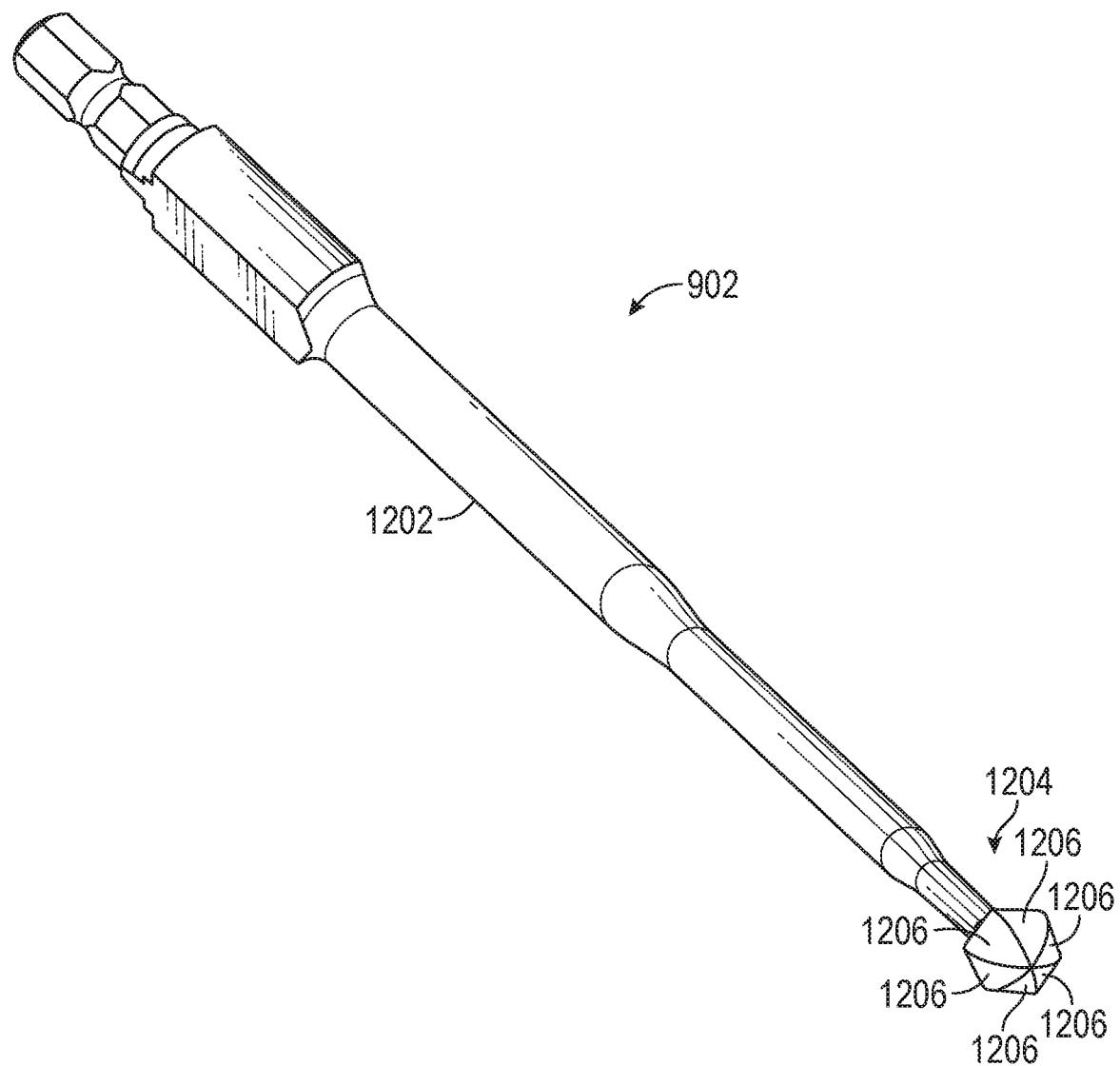
FIG. 12 shows a perspective view of a reamer driver in accordance with at least one example of the present disclosure.

FIG. 12 shows the reamer driver 902 in accordance with at least one example of the present disclosure. The reamer driver 902 can include a shaft 1202 and a reamer drive ball 1204. The reamer drive ball 1204 can include surfaces 1206. The surfaces 1206 can cooperate with the surfaces 1112 of the reamer socket 1110 such that rotation of the reamer driver 902 causes the reamer 904 to rotate. The shape of the surfaces 1206 can be similar to surfaces 502 described herein with respect to FIGS. 5-7.

The reamer socket 1110 and the reamer drive ball 1204 interface can enable the shaft 1206 of the reamer driver 902 to form a cone of approximately 62 degrees wide such that the reamer driver ball 1204 can freely articulate within the reamer socket 1110, thus resulting in a wide angle of excursion with no preferred relationship between a rotational axis of the reamer driver 902 and a rotational axis of the reamer peg 1106. This enables the reamer driver 902 to assume a wide range of angles of excursion relative to the rotational axis of the reamer peg 1106 to best fit the available wound access of individual patients.

The reamer driver 902, the reamer 904, and the base guide 906 can be manufactured from metals, polymers, ceramics, or any combination thereof. For example, the reamer driver 902 and the reamer 904 can be made of a metal and the base guide 906 can be made of a polymer. The reamer driver 902, the reamer 904, and the base guide 906 can be manufactured using any one or any combination of manufacturing techniques including, for example, machining, injection molding, overmolding, casting, welding, additive manufacturing, and the like. For instance, the reamer driver 902 and the reamer 904 can be machined from billets and the base guide 906 can be injection molded.

Figure 13:
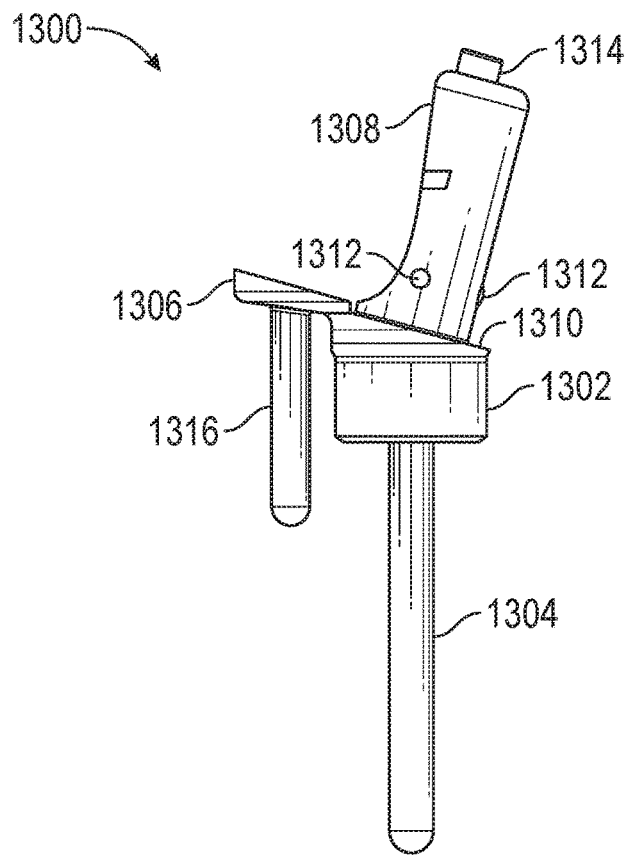
FIG. 13 shows a side view of a base guide in accordance with at least one example of the present disclosure.

FIG. 13 shows a base guide 1300 in accordance with at least one example of the present disclosure. The base guide 1300 can be used in conjunction with any of the reaming apparatuses disclosed herein. The base guide 1300 can include a base body 1302, a base peg 1304 that extends from the base body 1302, an extension 1306 that extends from the base body 1302, and a boss 1308. The boss 1308 can extend from an articulation surface 1310 of the base body 1302.

Figure 14:
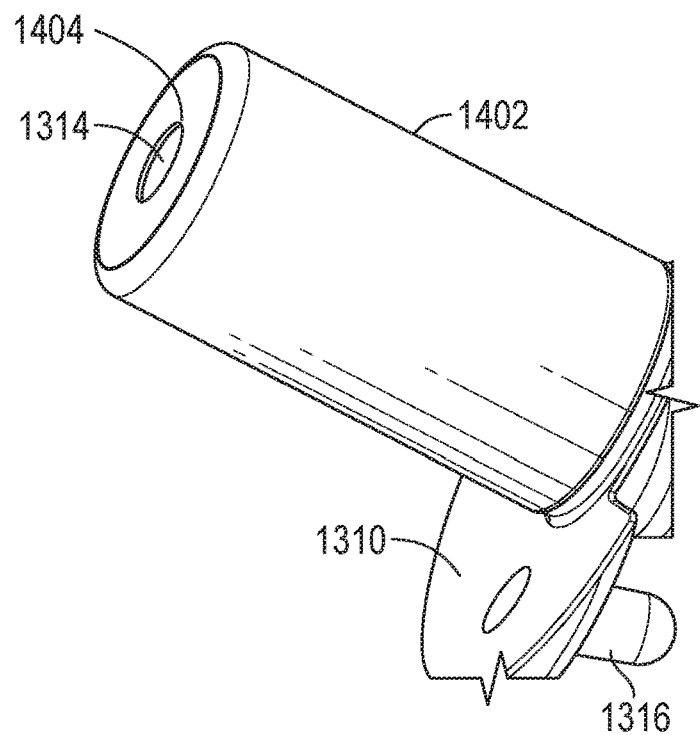
FIG. 14 shows a perspective view of a sleeve in accordance with at least one example of the present disclosure.

The boss 1308 can include one or more protrusions 1312 and a stub 1314. As shown in FIG. 14, a sleeve 1402 can be fitted onto the boss 1308. The protrusions 1312 can engage corresponding dimples or openings (not shown) located inside the sleeve 1402. The stub 1314 can penetrate an opening 1404. During installation and removal of the sleeve 1402, the opening 1404 can allow air to exit and pass into, respectively, the sleeve 1402 thereby preventing air pockets of a vacuum from forming and hindering installation or removal of the sleeve 1402. The opening 1404 can also act as a window to allow a surgeon to view inside the sleeve 1402. By viewing into the sleeve 1402 the surgeon can tell when the sleeve 1402 has sufficiently bottomed out on the boss 1308.

Returning to FIG. 13, an alignment peg 1316 can extend from the extension 1306. As disclosed herein, the alignment peg 1316 can be parallel to the base peg 1304. The parallel orientation. The alignment peg 1316 can help secure the base guide 1300 into bone and help prevent rotation of the base guide 1300 in bone.

Figure 15:
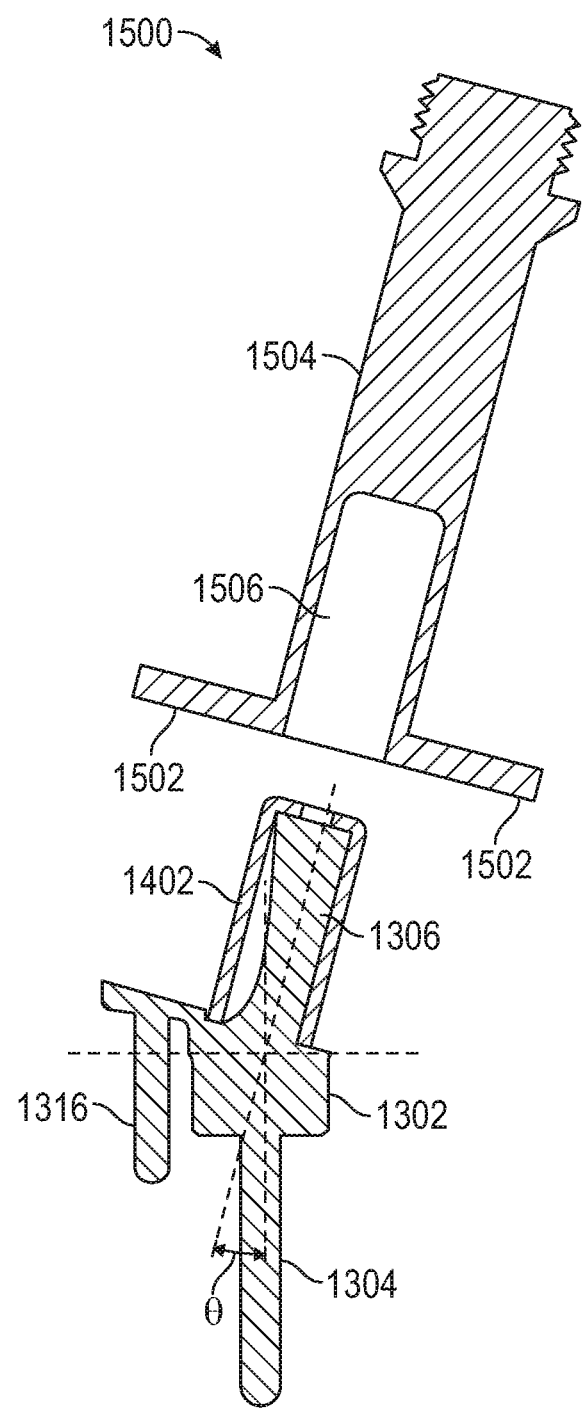
FIG. 15 shows a section view of a reaming apparatus in accordance with at least one example of the present disclosure.

As disclosed herein, the base guide 1300 can be used with the various reamers disclosed herein. For example, as shown in FIG. 15, the base guide 1300 can be coupled with a slotted reamer 1500. The slotted reamer 1500 can include cutting surfaces 1502 and a shaft 1504. The shaft 1504 can define a pocket 1506 that is sized to receive the sleeve 1402 or the boss 1306. During surgery, a surgeon can temporally implant the base guide 1300 and the slotted reamer 1500 can be used to ream a glenoid. As disclosed herein, the boss 1306 can be oriented at an angle θ relative to the base peg. Thus, as the slotted reamer 1500 rotates about the boss 1306, an angled surface can be prepared in the glenoid to receive a glenoid implant that has an angled surface configured to engage the glenoid.

The base guide 1300 and the sleeve 1402 can be manufactured from metals, polymers, ceramics, or any combination thereof. For example, the base guide can be made of a metal and the sleeve 1402 can be made of a polymer. The base guide 1300 and the sleeve 1402 can be manufactured using any one or any combination of manufacturing techniques including machining, injection molding, overmolding, casting, welding, and the like. For instance, the base guide 1300 can be machined from billets and the sleeve can be injection molded or overmolded onto the boss 1308.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

What is claimed is:

1. A reaming apparatus comprising:
   a base guide defining a base guide through bore, a base guide locking member extending outwardly from a first exterior surface of the base guide, and a second exterior surface defining a base guide articulating surface, the base guide articulating surface oriented at an angle relative to the base guide through bore;
   a reamer defining a reamer through bore and including a first surface defining a reamer gear, a second surface defining a plurality of reamer teeth, and a reamer articulating surface operable to allow rotation of the reamer on the base guide articulating surface;
   a reamer driver defining a reamer driver through bore and a reamer driver gear, the reamer driver gear sized to mesh with the reamer gear; and
   a guide shaft defining a reamer driver receiver and a guide shaft locking member operable to engage the base guide locking member to thereby secure the guide shaft to the base guide, wherein upon assembly of the reaming apparatus the base guide through bore, the reamer through bore, and the reamer driver through bore are coaxial.

2. The reaming apparatus of claim 1, wherein the angle the base guide through bore is oriented relative to the base guide articulating surface is non-orthogonal.

3. The reaming apparatus of claim 1, wherein the first surface defines a recessed portion and a sidewall, the reamer gear being defined by the sidewall.

4. The reaming apparatus of claim 1, wherein the reamer gear is defined at an oblique angle relative to the reamer articulating surface.

5. The reaming apparatus of claim 1, wherein the base guide further defines a boss, the reamer through bore sized to allow at least a portion of the boss to pass into the reamer through bore.

6. The reaming apparatus of claim 1, wherein the reamer driver gear and the reamer gear form an epicyclic gear train when assembled.

7. The reaming apparatus of claim 1, wherein the reamer gear and the reamer driver gear each include a plurality of complementary surfaces, the complementary surfaces configured to act together to form a geared system when assembled.

8. The reaming apparatus of claim 1, wherein the base guide locking member defines a locking peg.

9. The reaming apparatus of claim 1, wherein the guide shaft locking member defines an opening.

10. The reaming apparatus of claim 1, further comprising a guide rod configured to be connected to a glenoid and sized to be received within the base guide through bore, the reamer through bore, and the reamer driver through bore.

11. The reaming apparatus of claim 1, wherein the base guide further includes an alignment peg arranged parallel to and exterior the through bore.

12. A reaming system comprising:
    a plurality of base guides, each of the plurality of base guides defining a base guide through bore, a base guide locking member extending outwardly from a first exterior surface of the base guide, and a second exterior surface defining a base guide articulating surface, the base guide articulating surface oriented at an angle relative to the base guide through bore, wherein the angle the base guide articulating surface is oriented relative to the base guide through bore is different for each of the plurality of base guides;
    a reamer defining a reamer through bore and including a first surface defining a reamer gear, a second surface defining a plurality of reamer teeth, and a reamer articulating surface operable to allow rotation of the reamer on the base guide articulating surface;
    a reamer driver defining a reamer driver through bore and a reamer driver gear, the reamer driver gear sized to mesh with the reamer gear; and
    a guide shaft defining a reamer driver receiver and a guide shaft locking member operable to engage the base guide locking member thereby securing the guide shaft to the base guide, wherein upon assembly of a reaming apparatus the base guide through bore of one of the plurality of base guides, the reamer through bore, and the reamer driver through bore are coaxial.

13. The reaming system of claim 12, wherein the angle the base guide articulating surface is oriented relative to the base guide through bore for each of the plurality of base guides is non-orthogonal.

14. The reaming system of claim 12, wherein the reamer gear is defined at an oblique angle relative to the reamer articulating surface.

15. The reaming system of claim 12, wherein the reamer driver gear and the reamer gear form an epicyclic gear train when the reaming apparatus is assembled.

16. A reaming apparatus comprising:
    a base guide including a base guide through bore having a bore axis, a base guide articulating surface being proximal facing, and a base peg distal to the base guide articulating surface, the base peg having a peg axis, the base guide articulating surface oriented perpendicular to the bore axis, the peg axis oriented at an oblique angle relative to the bore axis;
    a reamer defining a reamer socket and a reamer articulation surface, the reamer including a reamer peg sized to be received in the base guide through bore and extending from the reamer articulation surface, and a plurality of cutting arms arranged perpendicular to the reamer peg; and
    a reamer driver defining a reamer drive ball configured to be received in the reamer socket and upon rotation of the reamer driver, cause the reamer to rotate.

17. The reaming apparatus of claim 16, wherein the reamer socket and the reamer drive ball each include a plurality of complementary surfaces, the complementary surfaces configured to act together to allow torque and rotation to be transmitted from the reamer driver to the reamer.

18. The reaming apparatus of claim 16, wherein the base guide comprises an alignment peg offset from the base peg and oriented parallel to the base beg.

19. The reaming apparatus of claim 16, wherein the base peg includes a plurality of fins that project from an exterior surface of the base peg.

20. The reaming apparatus of claim 16, wherein the base peg has a stepped profile.

\* \* \* \* \*